United States Patent [19]
DeCastro et al.

[11] Patent Number: 5,270,219
[45] Date of Patent: Dec. 14, 1993

[54] FLUID TRANSFER DEVICE

[75] Inventors: Aurora F. DeCastro, Union, Mich.; Surendra K. Gupta, Elkhart, Ind.

[73] Assignee: GDS Technology, Inc., Elkhart, Ind.

[21] Appl. No.: 9,405

[22] Filed: Jan. 27, 1993

Related U.S. Application Data

[63] Continuation of Ser. No. 795,594, Nov. 21, 1991, abandoned, which is a continuation-in-part of Ser. No. 379,829, Jul. 14, 1989, abandoned.

[51] Int. Cl.$^5$ .............................................. B01L 3/02
[52] U.S. Cl. ................... 436/180; 73/864.74; 141/329; 141/330; 422/100
[58] Field of Search ............ 422/100; 436/180; 141/329, 330; 73/864.74

[56] References Cited

U.S. PATENT DOCUMENTS

| | | | |
|---|---|---|---|
| 3,277,894 | 10/1966 | Alexander | 604/275 |
| 3,647,386 | 3/1972 | Gilford | 206/221 |
| 3,771,965 | 11/1973 | Grams | 422/72 |
| 3,941,171 | 3/1976 | Ogle | 141/309 |
| 4,256,120 | 3/1981 | Finley | 128/764 |
| 4,256,693 | 3/1981 | Kondo et al. | 422/57 |
| 4,296,786 | 10/1981 | Brignola | 141/309 |

FOREIGN PATENT DOCUMENTS 2026992 2/1980 United Kingdom ............... 141/330

*Primary Examiner*—Jill A. Johnston
*Attorney, Agent, or Firm*—Browdy and Neimark

[57] ABSTRACT

The fluid transfer device of the present invention is used for example, to provide access to a vacuum tube which is sealed with a stopper. The device has a cylindrical body with a top wall portion and first and second conduits fixed and extending therethrough. The first, or pouring conduit, and second, or pressure equilibrating conduit, extend generally in a parallel manner above and below the top wall portion, and their respective bottom portions are contained within the body of the hollow device. The pair of conduits are constructed and arranged within the body of the device to pierce and enter through the stopper of the sealed container to permit the delivery of fluid. Further, the device has a structure that can be easily and economically manufactured for disposable use.

21 Claims, 1 Drawing Sheet

FLUID TRANSFER DEVICE

FIELD OF THE INVENTION

The present application is a continuation of Ser. No. 07/795,594, filed Nov. 21, 1991, now abandoned which is a continuation-in-part of Ser. No. 07/379,829, filed Jul. 14, 1989, now abandoned, the entire contents of which are hereby incorporated by reference.

The present invention relates to a device for transferring fluids from a container or tube that has been filled with a fluid and that is sealed with a stopper. More particularly, the present invention relates to a fluid transfer device for transferring fluid in a safe and effective manner from a sealed container.

BACKGROUND OF THE INVENTION

Blood samples which are to be analyzed for constituents thereof such as glucose, uric acid, cholesterol, or drugs contained in the blood, such as theophylline, digoxin and phenytoin, are often collected from a patient in vacuum tubes. These vacuum tubes often contain an inert separator gel to separate the serum or plasma collected from the blood cells upon centrifugation. After centrifugation, the blood cells are thrown to the bottom of the tube, with the serum or plasma at the top of the tube and the separator gel being between the blood cells and the serum or plasma. The stopper is then removed manually from the vacuum tube to make the serum or plasma available for analysis.

While removing the stopper from a tube, the fluid, i.e., serum or plasma, in the tube can contact the hand of the operator directly as well as indirectly from fluid droplets which may be sprayed onto the surroundings as the stopper is forced out of the tube. Once the stopper is removed, the serum or plasma is poured into sample cups which then can be manually or automatically analyzed. The blood collecting tube is then restoppered, generally manually. The analyses can be performed by pipetting an exact amount of the serum or plasma into a reagent or test system. During all of these operations, the laboratory technician must manually remove and replace the stopper of the blood collection device, which often results in contact with the fluid in the collection device.

In other procedures, whole blood is used for the determination of chemical components of the blood or for determination of blood components. In this case, there is no requirement for separating the serum or plasma from red blood cells. The blood is merely collected from the patient into a vacuum tube which generally contains an anticoagulant to prevent clotting of the blood. The whole blood is subsequently removed from the blood collection tube for analysis by any conventional means. Again, before such analysis can be performed, the blood is poured out of the tube after first manually removing the stopper and, thus, presenting the same danger of accidentally splashing fluid on the operator, as discussed above.

Devices such as filers or membranes used to separate blood, which filters or membranes are not inside of a container, are shown in U.S. Pat. No. 4,256,693 and PCT/US96/02192. U.S. Pat. No. 4,256,693, deals with a filter layer capable of separating the cellular components from the non-cellular components in the blood. U.S. application PCT/US86/02192 deals with a process for separating the chemical components from cellular components of blood using a hydrophobic membrane treated with a surfactant. These blood separation techniques are not confined inside of a closed container. In addition, the device of the present invention is not a blood separation device per se.

U.S. Pat. No. 3,771,965 discloses a fluid sample tube assembly which includes a collection tube with a closure member sealing one end of the tube. The closure is provided with a cannula needle to receive fluid directly from a patient's body. The apparatus contains movable parts which, upon the application of external force, permit the sample to be drawn inside the tube for further processing without the need for opening the tube.

U.S. Pat. No. 3,647,386 discloses a sample processing container especially for use with serum or blood samples contained in a capillary tube which allows the capillary tube to be washed and its contents properly diluted.

U.S. Pat. No. 3,277,894 discloses a syringe package for injectable fluids comprising a barrel and a plunger to deliver fluids outside of a barrel, which barrel is not sealed.

U.S. Pat. No. 4,209,488 discloses a fluid collection system which can be used for separating blood serum or plasma from blood cells and particulate matter. The apparatus comprises an elongated hollow body which is closeable at both ends with a self-sealing septum near one end.

Brignola, in U.S. Pat. No. 4,296,786, discloses a fluid transfer device having a central disc portion and elongated cannulas or spikes disposed centrally thereof. The spikes are aligned and formed integrally with the disc of a suitable plastic material and are provided with a pair of axially extending transfer passages to permit fluid flow from one container to another. The cannulas terminate in tip portions which are tapered to facilitate penetration of a rubber stopper in a collection container. The fluid passage and the air venting passage are of different diameters. Various cover members are removed prior to use.

Cavazza, in British application 2,026,992 A discloses a taping device comprising a recessed capsule provided with an axially extending cylindrical body having faces parallel to each other and cut slanted to the body to provide a piercing top on each end of the body. The piercing top includes two parallel adjacent passages wherein the opposite outlets of one passage are axially offset from the corresponding outlets of the adjacent passage. The device is carried by a peripherally extending support which is matingly received in a suitably shaped recess provided in the bottom of the hollow capsule. A container closed by a rubber plug has a neck dimensioned to be received in the recess of the capsule.

Ogle, in U.S. Pat. No. 3,941,171, discloses a fluid transfer device comprising two parallel fluid passages, both carried by a flange which is generally perpendicular to the passages, wherein the two ends of the passages on each side of the flange are longitudinally displaced from one another and a medicament container having an open end closed by a rubber stopper. Each of the fluid passages can pierce the stopper. There is no means to protect a user from the sharp tips of the conduit ends.

Finley, in U.S. Pat. No. 4,256,120, discloses an evacuated blood sample collection device disposed in a conventional tube and needle holder 12 which includes a cylindrical portion having an opened end for receiving the collection device and a closed end for carrying a needle assembly having a double-ended needle cannula.

The needle is pointed at each end, extends longitudinally along the axis of the holder and has a distal end portion exterior to the holder and a proximately portion extending proximally within the cylindrical portion.

SUMMARY OF THE INVENTION

The fluid transfer device of the present invention is a unitized device. The length of the fluid transfer conduit and of the equilibration conduit are fixed and positioned in such a manner that the ratio of the lengths of these conduits is carefully controlled on the inside of the cylindrical body. However, outside of the cylindrical body, both conduits can be of any length, and can be of minimal length. This device is then placed on to a tube for fluid transfer therefrom.

The fluid transfer device of the present invention is designed to overcome the requirement for manually removing and replacing the stopper on closed or sealed containers which contain fluid, such as blood collecting or containing devices. The device of the present invention is constructed and arranged to permit the fluid to be transferred in a safe and effective manner to another container.

The present invention is directed to a unitary serum or plasma transfer device having a cylindrical body wherein the pouring and equilibrating conduits are fixed and have specific relative lengths whereby a user can easily and safely install the device onto a sealed blood container to introduce an atmospheric pressure source for subsequent serum or plasma transfer or extrusion.

The fluid transfer device of the present invention is used, for example, to provide access to a vacuum tube which is sealed with a stopper and which has been filled with blood from a patient. The device has a cylindrical body with a top wall portion and first and second conduits fixed and extending therethrough. The first, or pouring conduit, and second, or pressure equilibrating conduit, extend generally in a parallel manner above and below the top wall portion, and their respective bottom portions are contained within the body of the hollow device. The pair of conduits are constructed and arranged within the body of the device to pierce and enter through the stopper of the sealed container to permit the delivery of fluid. Further, the device has a structure that can be easily and economically manufactured for disposable use.

The pressure equilibrating conduit has a length which extends into the cylindrical body which is substantially longer than the length of the pouring conduit in the cylindrical body. In this fashion, the piercing bottom ends of the pouring and equilibrating conduits are protected by the cylindrical body, and the pressure within the sealed tube can be equilibrated with atmospheric pressure without any of the contents of the tube being released through the equilibrating conduit, only through the pouring conduit.

However, the length of either of the conduits which extends outside the tube has no requirements, and can be minimal.

The fluid transfer device of the present invention can, for example, be placed on top of a closed blood collection tube which can then be inverted to pour a desired volume of fluid through the first or pouring conduit. By avoiding manually opening and resealing the blood containing tube, the device of the present invention makes it possible to avoid any contact with the blood inside of the tube, therefore greatly reducing the threat of exposure to potentially hazardous blood, i.e., blood containing pathogenic agents such as HIV or hepatitis.

BRIEF DESCRIPTION OF THE INVENTION

These and other benefits of the present invention will become clear from the following nonlimiting description by reference to the drawings.

DETAILED DESCRIPTION OF THE INVENTION

Figure 2:
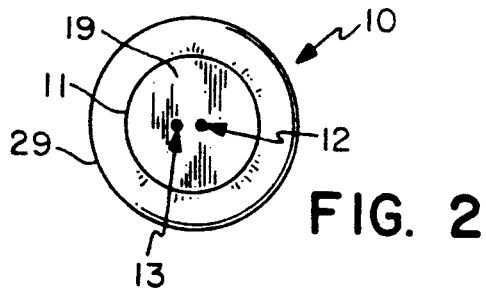
FIG. 2 is a top plan view of the device of FIG. 1.
Figure 1:
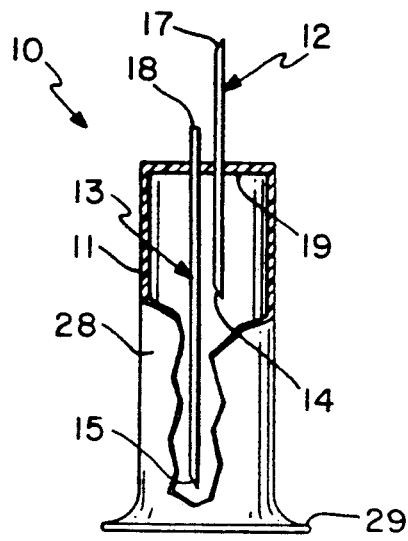
FIG. 1 is a schematic view of the fluid transfer device partially in cross-section and showing the pouring and pressure equilibration conduits.

FIGS. 1 and 2 show the fluid transfer device 10 of the present invention. The fluid transfer device 10 has first and second conduits, 12 and 13, respectively, which are fixed in and through the top wall 19 of the open, generally cylindrical body 11. The top and the conduits may be adhered together to form a unitary structure, or may be injection molded so as to form a unitary structure. The first or pouring conduit 12 has upper and lower portions which, respectively, extend above and below the top wall 19. The second or equilibrating conduit 13 extends generally parallel to conduit 12. The upper portion of conduit extends through top wall 19 and is in general shorter relative to conduit 12 and the lower portion extends lower than the bottom of tip 14 of conduit 12. However, the upper portions of conduits 12 or 13 can be minimally extended above the top of wall 19.

The channel or conduit, such as a needle, through which the sample is poured, is shown by reference numeral 12 and has a sharp point 14, to pierce and penetrate the stopper 24 which seal the blood collection device 20. Stoppers of this type are typically constructed of rubber or like elastomeric substances. The conduit 12 has a length long enough to clear completely the top of the stopper of the blood collection vacuum tube 20. Reference numeral 12 shows the conduit 13 which equilibrates the pressure between the inside of the tube 20 and the outside atmosphere so that the liquid can be easily poured out of the closed tube. The equilibrating conduit 13 is generally long enough to be close to the fluid level within tube 20 but above a separate gel 22 which keeps the blood cells disposed against the bottom of the tube 20 so that when the fluid containing tube 13 is inverted or tilted, the tip end 15 extends above the fluid level as shown in FIG. 4.

Alternatively, when the fluid inside the tube 20 is uncoagulated whole blood, conduit 13 is long enough so that when the tube is tilted or inverted the conduit end of tip 15 is above the fluid level, which in this case is near to the bottom of the tube. However, the device body 11, in both cases, has its side wall 28 long enough to extend beyond the bottom tip 15 of conduit 13. The bottom end tip 15 of conduit 13 and the bottom end tip of conduit 12 are preferably constructed of a rigid material such as metal, and are pointed and sharp so as to be able to pierce and penetrate the stopper 24.

Figure 3:
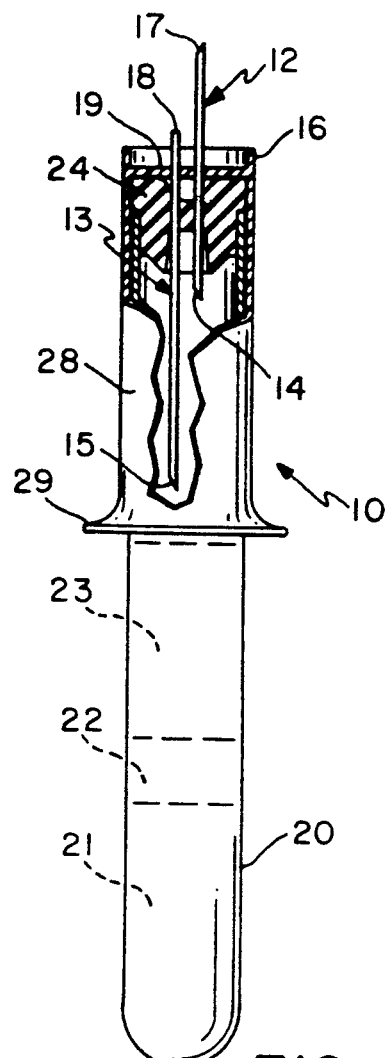
FIG. 3 is a schematic view of another embodiment of the device and shown partially in cross-section and in placement on a blood collection tube.
Figure 4:
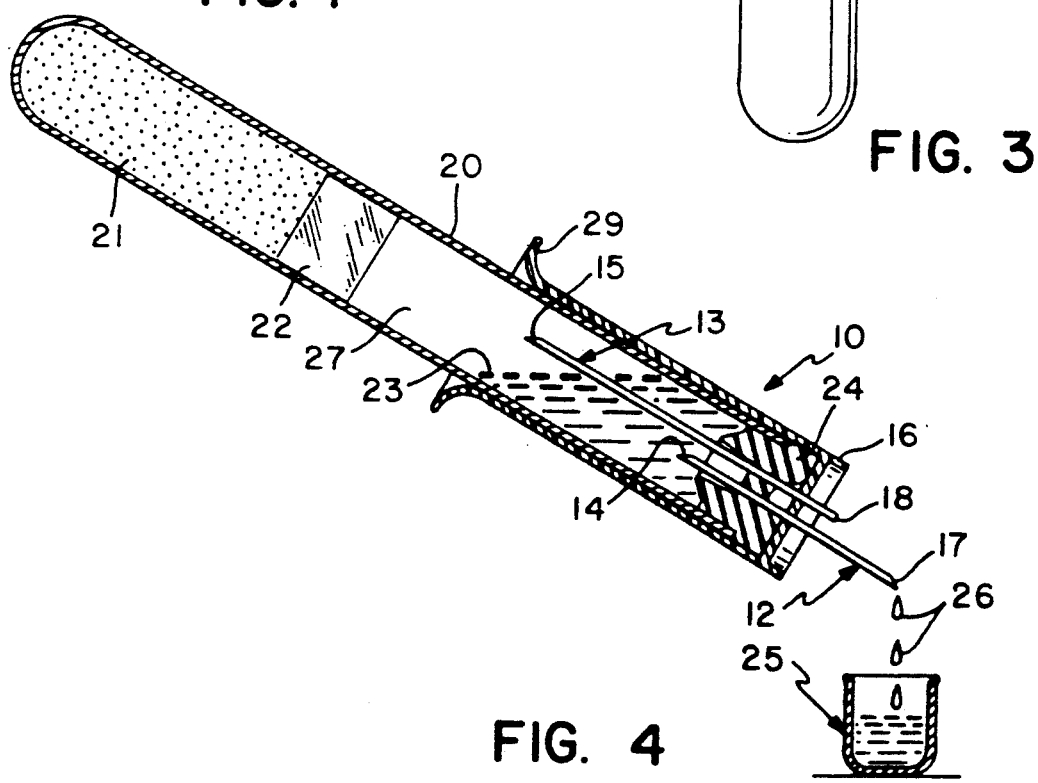
FIG. 4 is a schematic view in cross-section showing the fluid transfer device of FIG. 3 in use.

A peripheral lip 16 extending outwardly from body wall 19 of the body or casing 11 is shown in FIGS. 3 and 4, and is provided for catching any fluid droplets that may run down from the pouring conduit 12 after use.

Although the rim or lip 16 is preferred embodiment of the invention, it is not essential to the basic function of the device. The sharp conduit endings 14 and are further shown enclosed within the casing or cylindrical body 11 of the device 10 to protect the user from exposure thereto.

The cylindrical body, also referred to as the hollow body, the rigid body or hollow casing 11 of the device can be constructed or molded of a plastic, or a thermoplastic such as polypropylene or the like. The pouring and equilibrating conduits 12 and 13 preferably made of metal or like rigid material and molded or fixed in place through the top wall 19, making the device a unitary structure. The device 10 is preferably constructed of such materials and preferably molded to minimize production cost to provide a disposable device. The hollow body 11 may have a circumferentially flanged bottom portion to facilitate the placement of the device onto a sealed container.

FIGS. 3 and 4 show the device 10 in use and placed on top of a vacuum type blood collecting tube 20 and pushed through the stopper 24. FIG. 3 shows the device placed for use on a commercial blood collection vacuum tube. Such tubes are approximately 5 and 3/16 inches in length, 9/16 inches in diameter, and are provided with a stopper 24 approximately ⅜ inches long. The vacuum tube 20 is commercially available and typically has the above-mentioned dimension and usually contains an inert separating gel at the bottom. However, tubes of other dimensions can be used and the device scaled up or down appropriately. The tube 10, after collecting blood, is centrifuged to separate the blood cells from the serum. At the end of the centrifugation step, as shown in FIG. 3, the blood cells 21 are at the bottom of the tube, the serum 23 is at the top, and the separating gel 22 is at the interface between the blood cells and the serum. The separating gel 22 adheres to the interior wall of the tube so that when the tube 20 is inverted, the gel 22 does not move with respect to the tube 20. A device, 10, according to the invention as shown in FIG. 1, is placed on the blood collection tube 20. A device 10 having a pouring conduit of approximately 1 ½ inches in total length with ⅜ inch of this length being inside the device body has been found to be a convenient size for use with a conventional vacuum tube 20. The conduit 12 clears the stopper and protrudes through the bottom approximately ⅛ inch. The equilibrating conduit 13 is approximately 2 ⅛ inches inside of the device and protrudes behind the fluid 23 when the tube is inverted as shown in FIG. 4 and protrudes approximately ⅛ inches outside or through the top of the stopper 24.

Thus, the total length of the equilibrating conduit is approximately 2 ¼ inches. However, the lengths of conduits 12 and 13 within the confines of side wall 28 of the cylindrical body 11 are approximately ⅜ inch and 2 ⅛ inches, respectively. In other words, the relative lengths of the respective conduits 12 and 13 within the side wall 28 of cylindrical body 11 are such that the interior equilibrating portion so over 2.5 times longer than that of the pouring conduit. This conduit arrangement permits atmospheric pressure to be introduced into the space 27 above serum 23, as shown in FIG. 4, to extrude or pour sample 26 into analyzer cup 25.

The blood containing tube 20 is then inverted or tilted as shown in FIG. 4. The gel separator 22 and red blood cells 21 remain in place against the bottom of the tube and the serum 23 moves against the stopper 24. The equilibrating conduit 13 protrudes behind or above the serum 23. The serum 23, therefore, pours out through conduit 12 into an analyzer serum cup 25 for further analysis.

As noted above, the fluid transfer device of the present invention can also be used of the same purpose and in a similar manner if the tube 20 contains uncoagulated blood, or wherein the serum or plasma component has not been separated from the cellular components of the blood. Uncoagulated blood is obtained when the blood is drawn into tubes that contain EDTA, heparin, or any other anticoagulants. The device 10 will similarly allow the blood to be poured out of these blood collection tubes for further processing in blood assays.

The foregoing description of the specific embodiments will so fully reveal the general nature of the invention than others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A means for transferring fluid from a sealed vacuum tube, said means comprising:
   a) A sealed vacuum tube containing a liquid collected under vacuum;
   b) a unitary fluid transfer device comprising:
      (i) a hollow cylindrical body constructed and arranged to partially envelop a sealed vacuum tube and having a top portion, an open bottom portion and further having a predetermined length and diameter sufficiently long to protect piercing bottom ends of pouring and equilibrating conduits of the device;
      (ii) a pouring conduit fixed to said top portion of said cylindrical body and extending through said top portion and further having a sharp tipped bottom piercing end and extending downward a predetermined length into said hollow cylindrical body for insertion into a sealed vacuum tube below and adjacent a seal thereof; and
      (iii) an equilibrating conduit having a predetermined length and extending substantially along said predetermined cylindrical body length and being fixed to said cylindrical body portion and extending through said top portion whereby a top end of said equilibrating conduit is exposed to the atmosphere and further having a sharp tipped bottom piercing end extending to a point above the bottom portion of the hollow cylindrical body for substantial extension into a sealed vacuum tube to provide atmospheric pressure thereinto, whereby piercing bottom ends of said pouring and equilibrating conduits are protected by said cylindrical body, said equilibrating conduit extending below said top portion of said hollow cylindrical body at least approximately 2.5 times the length of said pouring conduit extending below said top portion of said hollow cylindrical body, said equilibrating conduit having a length able to extend beyond a liquid level in the vacuum tube when transferring liquid.

2. The fluid transfer device of claim 1, which is formed by injection molding so as to form a unitary structure.

3. The fluid transfer device of claim 1 wherein said pouring and equilibrating conduits are constructed of a rigid metallic material and molded in a fixed parallel position in said hollow body top portion.

4. The fluid transfer device of claim 1 wherein said pouring and equilibrating conduits have angled bottom ends with sharp tips.

5. The fluid transfer device of claim 1 wherein said hollow body further has a peripheral upper lip extending above said body top portion.

6. The fluid transfer device of claim 1 wherein said pouring conduit top end extends above said equilibrating conduit top end and wherein said equilibrating conduit bottom end extends below said pouring conduit bottom end.

7. The fluid transfer device of claim 1 wherein said hollow body is molded of a thermoplastic material.

8. The fluid transfer device of claim 1 wherein said pouring conduit has a length of approximately 1 $\frac{1}{8}$ inches and said equilibrating conduit has a length of approximately 2 $\frac{1}{4}$ inches.

9. The fluid transfer device of claim 1 wherein said hollow body has a circumferentially flanged bottom portion.

10. The fluid transfer device of claim 1 wherein said device is constructed and arranged to engage a sealed vacuum tube.

11. A fluid delivery system comprising a fluid delivery device and a sealed container or tube under vacuum, the contents of which container or tube are obtained under vacuum, said container or tube having a seal, said fluid delivery device constructed to remove fluids from said container or tube without removing the seal from said container or tube comprising a rigid body enclosure having a top portion and an open bottom portion and having a pouring conduit and an equilibrating conduit each extending through said top portion toward said open bottom portion, said pouring conduit and said equilibrating conduit each having a bottom tip to pierce the seal of said container or tube, and said equilibrating conduit extending below said top portion of said rigid member at least approximately 2.5 times the length of said pouring conduit extending below said top portion of said rigid member.

12. The device of claim 11 wherein the container is a vacuum tube.

13. The device of claim 11 wherein the rigid body enclosure is made of a thermoplastic material.

14. The device of claim 11 wherein the pouring conduit and the equilibrating conduit are each made of a metal and further have sharp tipped bottom ends for piercing the seal.

15. The device of claim 11 wherein the pouring conduit and the equilibrating conduit have angled bottom ends with sharp tips to pierce the seal.

16. The device of claim 11 wherein the rigid body enclosure has a circular cross-section.

17. The device of claim 11 wherein the rigid body enclosure has a top portion and a peripheral upper lip extending above said top portion.

18. (a) A means for transferring fluid comprising a container having a seal, the container containing a fluid introduced therein under vacuum; and (b) a unitary fluid transfer device comprising:

(1) a hollow cylindrical body constructed and arranged to partially envelop said container and having a top portion, an open bottom portion and further having a predetermined diameter and a length sufficiently long to protect equilibrating and pouring means of the device;

(2) pouring means located in said top portion of said cylindrical body and extending through said top portion through which liquid can be poured, said pouring means further having piercing means, said pouring means extending downward a predetermined length into said hollow cylindrical body for insertion into said sealed container through a seal in said container;

(3) equilibrating means having a predetermined length, said equilibrating means extending through said cylindrical body whereby a bottom portion of said equilibrating means extends through said hollow cylindrical body into said sealed container to introduce atmospheric pressure into liquid contained in said sealed container, whereby said equilibrating means extends below the length of said pouring means, said equilibrating means having a length extending into said cylindrical body that is at least approximately 2.5 times longer than the length of said pouring means.

19. The fluid transfer device according to claim 18 which is formed by injection molding so as to form a unitary structure.

20. A method for removing fluid from a sealed container, comprising:

(a) providing a sealed container containing fluid drawn into the container under vacuum, said container having a seal;

(b) introducing air into said sealed container by placing onto said sealed container a fluid transfer device in such a manner that the fluid transfer device in such a manner that the fluid transfer device pierces the seal on the sealed container;

said fluid transfer device comprising:

(1) a hollow cylindrical body constructed and arranged to partially envelop a container and having a top portion, an open bottom portion and further having a predetermined diameter and a length sufficiently long to protect equilibrating and pouring conduits of the device;

(2) a pouring conduit located in said top portion of said cylindrical body and extending through said top portion through which fluid can be poured, said pouring conduit further having a piercing end extending downward a predetermined length into said hollow cylindrical body for insertion into said sealed container through said seal in said container;

(3) an equilibrating conduit having a predetermined length, a top end and a bottom end, said equilibrating conduit extending through said cylindrical body whereby a top portion of said equilibrating conduit is exposed to the atmosphere, said equilibrating conduit extending through said hollow cylindrical body into said sealed container to introduce atmospheric pressure into said sealed container, said equilibrating conduit extending below said top portion of said hollow cylindrical body for a substantially longer length than the length of said pouring conduit extending below said top portion of said hollow cylindrical body;

(c) tilting said sealed container under vacuum so that the bottom of said equilibrating conduit extends beyond a level of the fluid in said container, whereby air enters said sealed container through said equilibrating conduit and fluid inside said sealed container is able to flow out of said sealed container through said pouring conduit.

21. The method according to claim 20, wherein said sealed container contains uncoagulated blood.

* * * * *